US010123990B2

(12) United States Patent
Eto et al.

(10) Patent No.: US 10,123,990 B2
(45) Date of Patent: Nov. 13, 2018

(54) METHOD FOR USING NOVEL HYDROXAMIC ACID DERIVATIVE AND ANTIBACTERIAL SUBSTANCE IN COMBINATION

(71) Applicant: TOYAMA CHEMICAL CO., LTD., Shinjuku-ku (JP)

(72) Inventors: Maki Eto, Toyama (JP); Tori Funatsu, Toyama (JP); Akiko Nakagawa, Toyama (JP); Masasuke Fujiwara, Toyama (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days.

(21) Appl. No.: 15/510,524

(22) PCT Filed: Sep. 11, 2015

(86) PCT No.: PCT/JP2015/075778
§ 371 (c)(1),
(2) Date: Mar. 10, 2017

(87) PCT Pub. No.: WO2016/039432
PCT Pub. Date: Mar. 17, 2016

(65) Prior Publication Data
US 2017/0296503 A1 Oct. 19, 2017

(30) Foreign Application Priority Data
Sep. 12, 2014 (JP) .................................. 2014-186569

(51) Int. Cl.
| *A61K 31/166* | (2006.01) |
| *A61K 31/325* | (2006.01) |
| *A61K 38/00* | (2006.01) |
| *A61K 31/407* | (2006.01) |
| *A61K 31/429* | (2006.01) |
| *A61K 31/496* | (2006.01) |
| *A61K 31/5383* | (2006.01) |
| *A61K 31/546* | (2006.01) |
| *A61K 31/7036* | (2006.01) |
| *A61K 31/167* | (2006.01) |
| *A61K 45/06* | (2006.01) |

(52) U.S. Cl.
CPC .......... *A61K 31/325* (2013.01); *A61K 31/166* (2013.01); *A61K 31/167* (2013.01); *A61K 31/407* (2013.01); *A61K 31/429* (2013.01); *A61K 31/496* (2013.01); *A61K 31/5383* (2013.01); *A61K 31/546* (2013.01); *A61K 31/7036* (2013.01); *A61K 38/00* (2013.01); *A61K 45/06* (2013.01); *Y02A 50/473* (2018.01)

(58) Field of Classification Search
CPC ............................ A61K 31/166; A61K 31/325
See application file for complete search history.

(56) References Cited

U.S. PATENT DOCUMENTS

| 9,862,676 | B2 * | 1/2018 | Shoji ..................... C07D 309/12 |
| 2013/0072677 | A1 | 3/2013 | Takashima et al. |
| 2016/0016895 | A1 | 1/2016 | Patterson et al. |
| 2016/0039751 | A1 | 2/2016 | Shoji et al. |

FOREIGN PATENT DOCUMENTS

| EP | 2 562 155 A1 | 2/2013 |
| EP | 2 975 022 A1 | 1/2016 |
| WO | 2004/062601 A2 | 7/2004 |
| WO | 2007/069020 A2 | 6/2007 |
| WO | 2008/154642 A2 | 12/2008 |
| WO | 2010/017060 A1 | 2/2010 |
| WO | 2010/031750 A1 | 3/2010 |
| WO | 2010/032147 A2 | 3/2010 |
| WO | 2011/132712 A1 | 10/2011 |
| WO | 2013/170165 A1 | 11/2013 |
| WO | 2014/142298 A1 | 9/2014 |

OTHER PUBLICATIONS

International Search Report dated Nov. 17, 2015, in PCT/JP2015/075778, filed Sep. 11, 2015.
Livermore, "Multiple Mechanisms of Antimicrobial Resistance in Pseudomonas aeruginosa: Our Worst Nightmare?", Antimicrobial Resistance, Mar. 1, 2002, p. 634-640.
Van Eldere, "Multicentre surveillance of Pseudomonas aeruginosa susceptibility patterns in nosocomial infections", Journal of Antimicrobial Chemotherapy, vol. 51, 2003, pp. 347-352.
Mikamo, et al., Surveillance on Pseudomonas aeruginosa Isolated in Gifu Prefecture (2004), Japanese Journal of Antibiotics, Oct. 2006, vol. 59, No. 5, p. 359-363 (with partial English translation).
Young, et al., "The envA Permeability/Cell Division Gene of *Escherichia coli* Encodes the Second Enzyme of Lipid A Biosynthesis", Journal of Biological Chemistry, vol. 270, No. 51, 1995, 9 pages.
Beall, et al., "Sequence Analysis, Transcriptional Organization, and Insertional Mutagenesis of the envA Gene of *Escherichia coli*", Journal of Bacteriology, vol. 169, No. 12, Dec. 1987, p. 5408-5415.
Szermerski, et al., "Synthesis, biological evaluation and molecular docking studies of benzyloxyacetohydroxamic acids as LpxC inhibitors", Bioorganic & Medicinal Chemistry, vol. 22, 2014, p. 1016-1028.

(Continued)

*Primary Examiner* — James D. Anderson
(74) *Attorney, Agent, or Firm* — Oblon, McClelland, Maier & Neustadt, L.L.P.

(57) ABSTRACT

Pharmacological compositions containing a hydroxamic acid derivative selected from (2S)-2-((4-((4-((1S)-1,2-dihydroxyethyl)phenyl)ethynyl)benzoyl)(methyl)amino)-N-hydroxy-N',2-dimethylmalonamide, (2S)-2-((4-((4-((1R)-1,2-dihydroxyethyl)phenyl)ethynyl)benzoyl)(methyl)amino)-N-hydroxy-N',2-dimethylmalonamide, and (2S)—N-hydroxy-2-((4-((4-((1S)-1-hydroxy-2-methoxyethyl)phenyl)ethynyl)benzoyl)(methyl)amino)-N',2-dimethylmalonamide, or a salt of said derivatives, and an antibiotic substance are useful in the treatment of gram-negative bacterial infections.

40 Claims, No Drawings

(56) References Cited

OTHER PUBLICATIONS

Extended European Search Report dated Mar. 22, 2018 issued in corresponding EP patent application No. 15840366.7.

* cited by examiner

METHOD FOR USING NOVEL HYDROXAMIC ACID DERIVATIVE AND ANTIBACTERIAL SUBSTANCE IN COMBINATION

TECHNICAL FIELD

The present invention relates to novel hydroxamic acid derivatives or the salt thereof, and the pharmaceutical compositions comprising an antimicrobial substance. The present invention also relates to treatment agents for Gram-negative bacterial infections, use of novel hydroxamic acid derivatives or the salt thereof for producing treatment agents, kits, and products.

BACKGROUND ART

Gram-negative bacteria have an outer membrane composed of a lipid bilayer, which does not exist in Gram-positive bacteria, and therefore tend to have stronger drug resistance, as compared to Gram-positive bacteria. Gram-negative bacteria are also known to have a plurality of drug efflux proteins, which are involved in drug resistance (Antimicrobial Resistance, 2002, Mar. 1, 34, pp. 634-640).

Among Gram-negative bacteria, *Pseudomonas aeruginosa*, in particular, has a strong tendency to show intrinsic resistance to various antimicrobial substances. In recent years, *Pseudomonas aeruginosa* which has gained resistance to carbapenem drugs, quinolone drugs, aminoglycoside drugs, or the like has been often isolated in medical settings (J. Antimicrob. Chemother., 2003, Vol. 51, pp. 347-352). Moreover, multi-drug resistant *Pseudomonas aeruginosa* has been isolated (Jpn. J. Antibiotics, 2006, Vol. 59, No. 5, pp. 355-363) and has posed worldwide major problems.

Multidrug resistant bacteria not only exhibit resistance to a plurality of antimicrobial substances, but also have the problem of limiting applicable antimicrobial substances. Thus, in addition to development of new medicaments, combination use with an existing antimicrobial substance is an important option. However, the theory of combination therapy directed against resistant bacteria has not been established, and satisfactory therapeutic effects have not been necessarily achieved (Kagaku Ryoho No Ryoiki, 2012, Vol. 28, No. 9).

UDP-3-O-acyl-N-acetylglucosamine deacetylase (LpxC) is an enzyme in charge of the synthesis of lipid A (the hydrophobic anchor of LPS, which is the constituent of the outer membrane).

Lipid A biosynthesis consists of reactions in 10 stages, and LpxC catalyzes the second stage to remove the acetyl group of UDP-3-O-acyl-N-acetylglucosamine (J. Biol. Chem., 1995, Vol. 270, pp. 30384-30391). Lipid A is a component essential for the formation of the outer membrane, and is indispensable for the survival of Gram-negative bacteria (J. Bacteriol., 1987, Vol. 169, pp. 5408-5415). LpxC is one of the rate-determining important enzymes during the process of lipid A biosynthesis, and is an indispensable enzyme for lipid A biosynthesis. Thus, a drug inhibiting the activity of LpxC is highly expected to be capable of becoming an antimicrobial agent effective against Gram-negative bacteria including *Pseudomonas aeruginosa*, particularly against drug resistant *Pseudomonas aeruginosa*, because such a drug has a mechanism of action different from those of conventional drugs.

Compounds having LpxC inhibitory activity have been known so far (Patent Documents 1 to 7).

PRIOR ART DOCUMENTS

Patent Documents

Patent Document 1: International Publication No. WO 04/062601 pamphlet
Patent Document 2: International Publication No. WO 07/069020 pamphlet
Patent Document 3: International Publication No. WO 08/154642 pamphlet
Patent Document 4: International Publication No. WO 10/031750 pamphlet
Patent Document 5: International Publication No. WO 10/017060 pamphlet
Patent Document 6: International Publication No. WO 10/032147 pamphlet
Patent Document 7: International Publication No. WO 11/132712 pamphlet

SUMMARY OF INVENTION

Problem to be Solved by the Invention

An object of the present invention is to provide a pharmaceutical composition useful for treatment of Gram-negative bacterial infections.

Means for Solving the Problem

Under such circumstances, the present inventors have intensively studied to find that pharmaceutical compositions that contain hydroxamic acid derivatives selected from (2S)-2-((4-((4-((1S)-1,2-dihydroxyethyl)phenyl)ethynyl)benzoyl)(methyl)amino)-N-hydroxy-N',2-dimethylmalonamide (sometimes referred to as "Compound A" hereinbelow), (2S)-2-((4-((4-((1R)-1,2-dihydroxyethyl)phenyl)ethynyl)benzoyl)(methyl)amino)-N-hydroxy-N',2-dimethylmalonamide (sometimes referred to as "Compound B" hereinbelow) and (2S)—N-hydroxy-2-((4-((1S)-1-hydroxy-2-methoxyethyl)phenyl)ethynyl)benzoyl)(methyl)amino)-N',2-dimethylmalonamide (sometimes referred to as "Compound C" hereinbelow), or salts thereof, and an antimicrobial substance exhibit potent antimicrobial activity and are useful for treatment of Gram-negative bacterial infections, and thereby have completed the present invention.

That is, the present invention provides the following.

[1] A pharmaceutical composition to be used for treatment of a Gram-negative bacterial infection, comprising a hydroxamic acid derivative selected from Compound A, Compound B and Compound C, or a salt thereof, and an antimicrobial substance.
[2] The pharmaceutical composition according to [1], wherein the hydroxamic acid derivative is Compound A.
[3] The pharmaceutical composition according to [1] or [2], wherein the antimicrobial substance is an antimicrobial agent.
[4] The pharmaceutical composition according to [3], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

[5] A treatment agent for a Gram-negative bacterial infection comprising a hydroxamic acid derivative selected from Compound A, Compound B and Compound C, or a salt thereof, wherein the treatment agent is used for combination with an antimicrobial substance.

[6] The treatment agent according to [5], wherein the hydroxamic acid derivative is Compound A.

[7] The treatment agent according to [5] or [6], wherein the antimicrobial substance is an antimicrobial agent.

[8] The treatment agent according to [7], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

[9] Use of a hydroxamic acid derivative selected from Compound A, Compound B and Compound C, or a salt thereof for producing a treatment agent for a Gram-negative bacterial infection to be used for combination with an antimicrobial substance.

[10] The use according to [9], wherein the hydroxamic acid derivative is Compound A.

[11] The use according to [9] or [10], wherein the antimicrobial substance is an antimicrobial agent.

[12] The use according to [11], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

[13] A kit to be used for treatment of a Gram-negative bacterial infection, the kit comprising a hydroxamic acid derivative selected from Compound A, Compound B and Compound C, or a salt thereof, and an antimicrobial substance.

[14] The kit according to [13], wherein the hydroxamic acid derivative is Compound A.

[15] The kit according to [13] or [14], wherein the antimicrobial substance is an antimicrobial agent.

[16] The kit according to [15], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

[17] A treatment agent for a Gram-negative bacterial infection, comprising an antimicrobial substance, the treatment agent being used for combination with a hydroxamic acid derivative selected from Compound A, Compound B and Compound C, or a salt thereof.

[18] The treatment agent according to [17], wherein the hydroxamic acid derivative is Compound A.

[19] The treatment agent according to [17] or [18], wherein the antimicrobial substance is an antimicrobial agent.

[20] The treatment agent according to [19], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

[21] A product comprising: (1) a treatment agent comprising a hydroxamic acid derivative selected from Compound A, Compound B and Compound C, or a salt thereof, (2) a container; and (3) an instruction, a description, a package insert, or a product label indicating that the treatment agent is used in combination with an antimicrobial substance to be used for treatment for a Gram-negative bacterial infection.

[22] The product according to [21], wherein the hydroxamic acid derivative is Compound A.

[23] The product according to [21] or [22], wherein the antimicrobial substance is an antimicrobial agent.

[24] The product according to [23], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

The present invention further provides the following.

[A] An instruction, a description, a package insert or a product label indicating that a treatment agent comprising a hydroxamic acid derivative selected from Compound A, Compound B, and Compound C, or a salt thereof is used in combination with an antimicrobial substance to be used for treatment for a Gram-negative bacterial infection.

[B] The instruction, the description, the package insert or the product label according to [A], wherein the hydroxamic acid derivative is Compound A.

[C] The instruction, the description, the package insert or the product label according to [A] or [B], wherein the antimicrobial substance is an antimicrobial agent.

[D] The instruction, the description, the package insert or the product label according to [C], wherein the antimicrobial agent is one or more selected from β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

Advantageous Effects of the Invention

The pharmaceutical composition has potent antimicrobial activity and is useful for treatment of Gram-negative bacterial infections.

MODE FOR CARRYING OUT THE INVENTION

The present invention will be described in detail below.
"%" means herein "% by mass," unless otherwise noticed.
Treatment means prophylaxis, therapy or the like against diseases.
Treatment agent means a substance to be provided for the purpose of prophylaxis, therapy or the like against diseases.
<Hydroxamic Acid Derivative>
Examples of the hydroxamic acid derivative used in the present invention include Compound A, Compound B, and Compound C, and Compound A is preferred.
The hydroxamic acid derivative can be produced in accordance with, for example, Production Examples described below.
When the hydroxamic acid derivative or a salt thereof has isomers (for example, optical isomers, geometrical isomers, and tautomers), the present invention encompasses these isomers and also encompasses their solvates, hydrates, and crystals of various forms.
Examples of the salt of the hydroxamic acid derivative include salts with alkali metal, such as sodium and potassium; salts with alkaline earth metal, such as calcium and magnesium; ammonium salts; and salts with nitrogen-containing organic bases, such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Preferred salts among the salts described above include pharmacologically acceptable salts.

Administration methods, doses, and frequency of administration of the hydroxamic acid derivative or a salt thereof may be selected as appropriate depending on the age, body weight, and condition of a patient. Usually for adults, it may be orally or parenterally (for example, by injection, infusion, or administration to the rectal site) administered in an amount of 0.01 to 1000 mg/kg/day in one to several portions.

<Antimicrobial Substance>

Examples of the antimicrobial substance used in the present invention include antimicrobial agents and antimicrobial proteins, and antimicrobial agents are preferred.

Examples of the antimicrobial agent include β-lactam antimicrobial agents, aminoglycoside antimicrobial agents, new quinolone antimicrobial agents, glycopeptide antimicrobial agents, rifamycin antimicrobial agents, lincomycin antimicrobial agents, and macrolide antimicrobial agents.

Examples of the β-lactam antimicrobial agent include penicillin antimicrobial agents, penicillin antimicrobial agents combined with a β-lactamase inhibitor, cephem antimicrobial agents, cephem antimicrobial agents combined with a β-lactamase inhibitor, carbapenem antimicrobial agents, carbapenem antimicrobial agents combined with a β-lactamase inhibitor, monobactam antimicrobial agents, and penem antimicrobial agents, and penicillin antimicrobial agents, penicillin antimicrobial agents combined with a β-lactamase inhibitor, cephem antimicrobial agents, cephem antimicrobial agents combined with aβ-lactamase inhibitor, and carbapenem antimicrobial agents are preferred.

Examples of the penicillin antimicrobial agent include benzylpenicillin, penicillin O, penicillin V, penicillin G, methicillin, oxacillin, cloxacillin, dicloxacillin, carbenicillin, bacampicillin, ticarcillin, azlocillin, mezlocillin, amoxicillin, sultamicillin, talampicillin, lenampicillin, cyclacillin, pivmecillinam, aspoxicillin, ampicillin and piperacillin, and piperacillin is preferred.

Examples of the penicillin antimicrobial agent combined with a β-lactamase inhibitor include ampicillin-sulbactam combination agents, clavulanic acid-amoxicillin combination agents, and piperacillin-tazobactam combination agents, and piperacillin-tazobactam combination agents are preferred.

Examples of the cephem antimicrobial agent include cefazolin, cephalothin, cephapirin, cephalexin, cefadroxil, cephaloridine, ceftezole, cefroxadine, cefamandole, cefuroxime, cefonicid, ceforanide, cefaclor, cefprozil, cefpodoxime, loracarbef, ceftriaxone, cefotaxime, ceftizoxime, cefoperazone, cefsulodin, ceftibuten, cefixime, cefetamet, cefditoren pivoxil, cefpirome, cefoxitin, cefotetan, cefmetazole, cefbuperazone, cefminox, latamoxef, flomoxef, cefotiam, cefpiramide, cefmenoxime, cefozopran, cefatrizine, cefdinir, cefteram pivoxil, cefcapene pivoxil, ceftolozane, ceftaroline, cefradine ceftolozane, ceftazidime, and cefepime, and ceftazidime and cefepime are preferred.

Examples of the cephem antimicrobial agent combined with a β-lactamase inhibitor include cefoperazone-sulbactam combination agents, ceftazidime-avibactam combination agents, ceftaroline-avibactam combination agents, and ceftolozane-tazobactam combination agents.

Examples of the carbapenem antimicrobial agent include imipenem, panipenem, biapenem, doripenem, ertapenem, tebipenem, tomopenem, saftrinem, lenapenem, and meropenem, and doripenem, imipenem, and meropenem are preferred.

Examples of the carbapenem antimicrobial agent combined with a β-lactamase inhibitor include imipenem-MK-7655 combination agents and biapenem-RPX7009 combination agents.

Examples of the monobactam antimicrobial agent include aztreonam and carumonam.

Examples of the penem antimicrobial agent include faropenem and sulopenem.

Examples of the aminoglycoside antimicrobial agent include streptomycin, neomycin, kanamycin, paromycin, gentamicin, tobramycin, netilmicin, spectinomycin, sisomicin, dibekalin, bekanamycin, ribostamycin, astromicin, arbekacin, plazomicin, isepamicin, and amikacin, and amikacin is preferred.

Examples of the new quinolone antimicrobial agent include nalidixic acid, oxolinic acid, piromidic acid, pipemidic acid, norfloxacin, pefloxacin, enoxacin, ofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin, garenoxacin, prulifloxacin, tosufloxacin, besifloxacin, finafloxacin, delafloxacin, abafloxacin, zabofloxacin, nemonoxacin, pazufloxacin, ciprofloxacin, and levofloxacin, and ciprofloxacin, pazufloxacin, and levofloxacin are preferred.

Examples of the glycopeptide antimicrobial agent include vancomycin, telavancin, and teicoplanin, and vancomycin and teicoplanin are preferred.

An example of the rifamycin antimicrobial agent is rifampicin.

An example of the lincomycin antimicrobial agent include clindamycin.

Examples of the macrolide antimicrobial agent include erythromycin and azithromycin.

Examples of the antimicrobial protein include lysozyme and its salts.

Examples of the salt of lysozyme include salts with a mineral acid such as hydrochloric acid, hydrobromic acid, nitric acid, and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid, and trifluoroacetic acid; and salts with a sulfonic acid such as methanesulfonic acid, benzenesulfonic acid, p-toluenesulfonic acid, mesitylene sulfonic acid, and naphthalene sulfonic acid.

Preferred salts among the salts described above include pharmacologically acceptable salts.

<Combination>

In the present invention, a hydroxamic acid derivative or a salt thereof and an antimicrobial substance are used in combination.

Combination herein means a combination of a hydroxamic acid derivative or a salt thereof and an antimicrobial substance and encompasses cases where the hydroxamic acid derivative or a salt thereof is administered with an antimicrobial substance simultaneously, separately, or in a specific order and cases where they are administered in the form of a mixture (combination agent). In other words, "combination" not only means that the administration timing of a hydroxamic acid derivative or a salt thereof and of an antimicrobial substance are the same, but also encompasses cases where a hydroxamic acid derivative or a salt thereof and an antimicrobial substance are administered during an administration schedule. The administration routes of a hydroxamic acid derivative or a salt thereof and of an antimicrobial substance may be the same or different.

<Gram-Negative Bacterial Infection>

Examples of the Gram-negative bacterial infection include infections by Gram-negative bacteria such as those from the group consisting of the genus *Pseudomonas*, the genus *Stenotrophomonas*, the genus *Burkholderia*, the genus *Acinetobacter*, the genus *Alcaligenes* the genus *Legionella*, the genus *Bordetella*, the genus *Brucella*, the genus *Bacteroides*, the genus *Fusobacterium*, the genus *Neisseria*, the genus *Moraxella*, the genus *Campylobacter*, the genus *Helicobacter*, the genus *Vibrio*, the genus *Aeromonas*, the genus *Haemophilus*, the genus *Yersinia*, the genus *Chryseobacterium*, the genus *Elizabethkingia*, the genus *Flavobacterium*, and the family Enterobacteriaceae.

<Pharmaceutical Composition>

The pharmaceutical composition of the present invention contains a hydroxamic acid derivative or a salt thereof and an antimicrobial substance and is used for treatment of Gram-negative bacterial infections.

The pharmaceutical composition may contain pharmaceutical aids usually used for formulation, such as an excipient, a carrier, and a diluent.

The pharmaceutical composition may be formulated into forms such as tablets, capsules, powders, syrups, granules, pills, suspensions, emulsions, solutions, powder preparations, suppositories, eye drops, nasal drops, ear drops, patches agents, ointments or injections.

The administration route is not particularly limited, and the pharmaceutical composition may be administered intravenously, orally, intramuscularly, subcutaneously, by inhalation, by spraying, or by other administration routes.

The hydroxamic acid derivative or a salt thereof may be administered with an antimicrobial substance simultaneously, separately, or in a specific order.

The hydroxamic acid derivative is as described above.

The antimicrobial substance is as described above.

The Gram-negative bacterial infection is as described above.

<Treatment Agent>

The treatment agent of the present invention contains a hydroxamic acid derivative or a salt thereof, is used in combination with an antimicrobial substance, and is used for treatment of Gram-negative bacterial infections.

The administration route of the treatment agent is not particularly limited, and the treatment agent may be administered intravenously, orally, intramuscularly, subcutaneously, by inhalation, by spraying, or by other administration routes. Additionally, the treatment agent may be administered with an antimicrobial substance simultaneously, separately, or in a specific order.

In another embodiment, the treatment agent of the present invention contains an antimicrobial substance, is used in combination with a hydroxamic acid derivative or a salt thereof, and is used for treatment of Gram-negative bacterial infections.

The administration route of the treatment agent is not particularly limited, and the treatment agent may be administered intravenously, orally, intramuscularly, subcutaneously, by inhalation, by spraying, or by other administration routes. Additionally, the treatment agent may be administered with a hydroxamic acid derivative or a salt thereof simultaneously, separately, or in a specific order.

The hydroxamic acid derivative is as described above.

The antimicrobial substance is as described above.

The Gram-negative bacterial infection is as described above.

<Use>

The present invention includes use of a hydroxamic acid derivative or a salt thereof for producing a treatment agent for Gram-negative bacterial infections used for combination with an antimicrobial substance.

The hydroxamic acid derivative is as described above.

The antimicrobial substance is as described above.

The Gram-negative bacterial infection is as described above.

<Kit>

The kit of the present invention comprises a hydroxamic acid derivative or a salt thereof and an antimicrobial substance in a single package and is used for treatment of Gram-negative bacterial infections. The kit may additionally comprise tools for administration, an instruction, a description, a package insert, or a product label, for example. The kit is particularly useful when the hydroxamic acid derivative or a salt thereof and the antimicrobial substance are administered in different administration routes or when the dose of individual components is preferably set by a physician.

The administration route of the hydroxamic acid derivative or a salt thereof is not particularly limited, and the treatment agent may be administered intravenously, orally, intramuscularly, subcutaneously, by inhalation, by spraying, or by other administration routes. Additionally, the hydroxamic acid derivative or a salt thereof may be administered with an antimicrobial substance simultaneously, separately, or in a specific order.

The hydroxamic acid derivative is as described above.

The antimicrobial substance is as described above.

The Gram-negative bacterial infection is as described above.

<Product>

The product of the present invention comprises (1) a treatment agent comprising a hydroxamic acid derivative or a salt thereof; (2) a container; and (3) an instruction, a description, a package insert, or a product label indicating that the treatment agent is used in combination with an antimicrobial substance to be used for treatment for a Gram-negative bacterial infection.

The product of the present invention is used for treatment of Gram-negative bacterial infections.

The container refers to those enclosing the treatment agent comprising a hydroxamic acid derivative or a salt thereof, and examples include cans, bottles, boxes, ampules, vials, plastic bags, strip package (SP) sheets, and press-through-package (PTP) sheets.

The hydroxamic acid derivative is as described above.

The antimicrobial substance is as described above.

The Gram-negative bacterial infection is as described above.

The pharmaceutical composition, treatment agent, kit, and product of the present invention are useful for treatment of Gram-negative bacterial infections. These are useful particularly for treatment of infections by *Escherichia coli, Klebsiella pneumoniae, Pseudomonas aeruginosa, Acinetobacter baumannii*, and/or *Stenotrophomonas maltophilia*. Especially, these are useful for treatment of infections by *Acinetobacter haumannii*.

The pharmaceutical composition, treatment agent, kit, and product of the present invention enable treatment of severer Gram-negative bacterial infections. Furthermore, when a reduced amount of each medicament to be used is administered, a potent antimicrobial effect is exhibited to thereby enable reduction in side effects of each of the medicaments.

The present invention will be now described referring to Test Examples, but the present invention is not intended to be limited to these.

Each abbreviation has the following meaning.
AMK: amikacin
CAZ: ceftazidime
CFPM: cefepime
CPFX: ciprofloxacin
DRPM: doripenem
IPM: imipenem
LVFX: levofloxacin
MEPM: meropenem
PZFX: pazufloxacin
PIPC: piperacillin
TAZ: tazobactam
TEIC: teicoplanin
VCM: vancomycin Test Example 1 Test to Evaluate *Pseudomonas Aeruginosa* LpxC Enzyme Inhibitory Activity Compound A, Compound B and Compound C were used as a Test Compound.

The *Pseudomonas aeruginosa* LpxC enzyme activity was measured by reacting LpxC with its substrate UDP-3-O—(R-3-hydroxydecanoyl)-N-acetylglucosamine and measuring the amount of the reaction product by the quantification of an amino group present in the product. This measurement was carried out according to a method described in, for example, International Publication No. WO 11/132712 pamphlet or a method similar thereto.

Specifically, to the *Pseudomonas aeruginosa* LpxC enzyme (which was obtained by preparing chromosomal DNA from *Pseudomonas aeruginosa*, obtaining the *Pseudomonas aeruginosa* LpxC gene by PCR (polymerase chain reaction) using LpxC-specific primers, and incorporating this gene into a vector, followed by gene expression using *Escherichia coli*), 20 μmol/L UDP-3-O—(R-3-hydroxydecanoyl)-N-acetylglucosamine (Wako Pure Chemical Industries, Ltd.) was added, and the mixture was incubated at 25° C. for 1 hour. This reaction was carried out in a 40 mmol/L HEPES buffer solution (pH 8.0) containing 0.02% Brij 35 and 80 μmol/L dithiothreitol. The reaction was terminated by the addition of 20% acetic acid (final concentration: 0.95%) to the reaction solution. Then, fluorescamine (final concentration: 1.6 mg/mL) dissolved in anhydrous dioxane was added thereto. The amount of the reaction product was detected at an excitation wavelength/fluorescence wavelength=390 nm/495 nm. Each test compound was allowed to coexist at various concentrations in the reaction to obtain an inhibition curve. From the inhibition curve, the concentration at which the test compound inhibited 50% of the amount of the reaction product ($IC_{50}$ value) was determined and used as an index for *Pseudomonas aeruginosa* LpxC enzyme inhibitory activity.

As a result, all the $IC_{50}$ values of the test compounds were less than 50 nM.

The test compounds exhibited an excellent *Pseudomonas aeruginosa* LpxC enzyme inhibitory activity.

Test Example 2 Test to Evaluate Antibacterial Activity

The minimum inhibitory concentration (MIC) was measured according to the CLSI (Clinical and Laboratory Standards Institute) standard method using a broth microdilution method given below.

A liquid dilution method was used to evaluate interactions between test compounds and antimicrobial substances.

Compounds A, B and C were used as a test compound.

As the antimicrobial substances, meropenem (commercially available product), imipenem (commercially available product), doripenem (commercially available product), cefepime (commercially available product), amikacin (commercially available product), levofloxacin (Chem-Impex International, Inc.), ciprofloxacin (LKT Laboratories, Inc.), piperacillin (commercially available product), piperacillin/tazobactam (tazobactam: TAIHO PHARMACEUTICAL CO., LTD.), vancomycin (commercially available product), ceftazidime (commercially available product), pazufloxacin (TOYAMA CHEMICAL CO., LTD.), teicoplanin (commercially available product), and human lysozyme (Wako Pure Chemical Industries, Ltd.) were used.

As the bacteria, the *Pseudomonas aeruginosa* S-3097 strain, the *Pseudomonas aeruginosa* S-2994 strain, the *Klebsiella pneumoniae* Y-891 strain, the *Klebsiella pneumoniae* BAA1899 strain, the *Escherichia coli* TK-1428 strain, the *Escherichia coli* TK-1537 strain, the *Stenotrophomonas mahophiha* PM-171 strain, the *Stenotrophomonas maltophilia* NBRC13692 strain, the *Acinetobacter baumannii* BAA-1791 strain, and the *Acinetobacter baumannii* BAA-1794 strain were used.

The subject bacteria cultured overnight in a Mueller-Hinton agar medium were scraped off and suspended to correspond to a 0.5 McFarland standard. This suspension was diluted 10-fold to be used as an inoculum liquid. To cation-adjusted Mueller-Hinton media containing the test compound singly, containing each antimicrobial substance singly, and containing the test compound and each antimicrobial substance, 0.005 mL of the inoculum liquid was inoculated and cultured at 35° C. for 18 to 20 hours. The minimum agent concentration at which no bacterial growth was observed with the naked eye was taken as the MIC.

The antimicrobial activity of the test compound singly, of each antimicrobial substance singly, and of the combination of the test compound and each antimicrobial substance were evaluated, and FIC indices were calculated.

The FIC index was taken as the minimum value of the values determined according to: (MIC value when used in combination with the test compound/MIC value when the test compound is used singly)+(MIC value when used in combination with the antimicrobial substance/MIC value when the antimicrobial substance is used singly).

It was determined that there was a synergistic effect as a result of the combination of both agents in the case where the FIC index was 0.5 or less. It was determined that there was an additive effect in the case where the FIC index was 0.51 or more and 1 or less (Diagnostic Microbiology and Infectious Disease, 2004, Vol. 49, p. 197).

The results of the combinations of Compound A with the antimicrobial substances are shown in Tables 1 to 10.

TABLE 1

Pseudomonas aeruginosa S-3097 strain

| Composition | Compound A MEPM | Compound A IPM | Compound A CFPM | Compound A AMK | Compound A LVFX | Compound A CPFX |
|---|---|---|---|---|---|---|
| FIC index | 0.50 | 1.00 | 0.38 | 0.56 | 0.75 | 1.00 |

TABLE 2

Pseudomonas aeruginosa S-2994 strain

| Composition | Compound A IPM | Compound A AMK |
|---|---|---|
| FIC index | 0.19 | 0.50 |

TABLE 3

Klebsiella pneumoniae Y-891 strain

| Composition | Compound A MEPM | Compound A PIPC/TAZ* | Compound A CFPM | Compound A CPFX |
|---|---|---|---|---|
| FIC index | 0.56 | 0.31 | 0.63 | 1.00 |

*TAZ = 4 µg/mL

TABLE 4

Klebsiella pneumoniae BAA-1899 strain

| Composition | Compound A CFPM | Compound A MEPM | Compound A VCM | Compound A CAZ | Compound A AMK |
|---|---|---|---|---|---|
| FIC index | 0.56 | 0.56 | ≤0.75 | ≤0.75 | ≤0.31 |

TABLE 5

Escherichia coli TK-1428 strain

| Composition | Compound A PIPC | Compound A CAZ | Compound A MEPM | Compound A AMK |
|---|---|---|---|---|
| FIC index | 0.75 | ≤0.52 | 0.62 | 0.63 |

TABLE 6

Escherichia coli TK-1537 strain

| Composition | Compound A CFPM | Compound A LVFX |
|---|---|---|
| FIC index | 1.00 | 0.50 |

TABLE 7

Stenotrophomonas maltophilia PM-171 strain

| Composition | Compound A MEPM | Compound A AMK | Compound A CFPM | Compound A LVFX |
|---|---|---|---|---|
| FIC index | 0.50 | ≤0.25 | 0.50 | 1.00 |

TABLE 8

Stenotrophomonas maltophilia NBRC13692 strain

| Composition | Compound A CFPM | Compound A MEPM | Compound A AMK |
|---|---|---|---|
| FIC index | 0.50 | ≤0.75 | 1.00 |

TABLE 9

Acinetobacter baumannii BAA-1791 strain

| Composition | Compound A CFPM | Compound A MEPM | Compound A IPM | Compound A DRPM | Compound A LVFX | Compound A VCM |
|---|---|---|---|---|---|---|
| FIC index | ≤0.13 | ≤0.13 | ≤0.13 | ≤0.13 | ≤0.56 | ≤0.05 |

TABLE 9-continued

*Acinetobacter baumannii* BAA-1791 strain

| Composition | Compound A PIPC/TAZ | Compound A CAZ | Compound A PZFX | Compound A AMK | Compound A TEIC |
|---|---|---|---|---|---|
| FIC index | ≤0.06 | ≤0.31 | ≤0.31 | ≤0.19 | ≤0.08 |

TABLE 10

*Acinetobacter baumannii* BAA-1794 strain

| Composition | Compound A CPFX | Compound A LVFX | Compound A IPM | Compound A CFPM | Compound A PIPC/TAZ* |
|---|---|---|---|---|---|
| FIC index | ≤0.38 | ≤0.75 | ≤0.13 | ≤0.31 | ≤0.56 |
| Composition | Compound A CAZ | Compound A MEPM | Compound A AMK | Compound A TEIC | Compound A lysozyme |
| FIC index | ≤0.27 | ≤0.08 | ≤0.28 | ≤0.09 | ≤0.25 |

*TAZ = 4 μg/mL

The results of the combinations of Compound B with each antimicrobial substance are shown in Tables 11 to 17.

TABLE 11

*Pseudomonas aeruginosa* S-3097 strain

| Composition | Compound B PIPC/TAZ* | Compound B CFPM | Compound B MEPM | Compound B IPM | Compound B AMK |
|---|---|---|---|---|---|
| FIC index | 0.25 | 0.50 | 0.63 | 1.00 | 035 |

*TAZ = 4 μg/mL

TABLE 12

*Pseudomonas aeruginosa* S-2994 strain

| Composition | Compound B IPM | Compound B AMK |
|---|---|---|
| FIC index | 0.38 | 0.75 |

TABLE 13

*Klebsiella pneumoniae* BAA-1899 strain

| Composition | Compound B CFPM | Compound B MEPM | Compound B LVFX | Compound B AMK | Compound B VCM |
|---|---|---|---|---|---|
| FIC index | 0.56 | 0.56 | ≤1.00 | 0.63 | ≤0.75 |

TABLE 14

*Escherichia coli* TK-1428 strain

| Composition | Compound B PIPC/TAZ* |
|---|---|
| FIC index | 1.00 |

*TAZ = 4 μg/mL

TABLE 15

*Escherichia coli* TK-1537 strain

| Composition | Compound B CFPM | Compound B MEPM | Compound B LVFX |
|---|---|---|---|
| FIC index | 1.00 | 0.50 | 1.00 |

TABLE 16

*Stenotrophomonas maltophilia* NBRC13692 strain

| Composition | Compound B CFPM | Compound B MEPM | Compound B AMK |
|---|---|---|---|
| FIC index | 0.75 | ≤0.38 | 0.53 |

TABLE 17

*Acinetobacter baumannii* BAA-1791 strain

| Composition | Compound B CFPM | Compound B MEPM | Compound B LVFX | Compound B AMK | Compound B VCM |
|---|---|---|---|---|---|
| FIC index | ≤0.25 | ≤0.14 | ≤0.75 | ≤0.25 | ≤0.13 |

The results of the combinations of Compound C with each antimicrobial substance are shown in Tables 18 to 24.

TABLE 18

*Pseudomonas aeruginosa* S-3097 strain

| Composition | Compound C PIPC/TAZ* | Compound C CFPM | Compound C MEPM | Compound C IPM | Compound C AMK |
|---|---|---|---|---|---|
| FIC index | 0.25 | 0.63 | 0.50 | 1.00 | 0.75 |

*TAZ = 4 μg/mL

TABLE 19

*Pseudomonas aeruginosa* S-2994 strain

| Composition | Compound C IPM | Compound C AMK |
|---|---|---|
| FIC index | 0.25 | 0.38 |

TABLE 20

*Klebsielia pneumoniae* BAA-1899 strain

| Composition | Compound C CFPM |
|---|---|
| FIC index | 0.50 |

TABLE 21

*Escherichia coli* TK-1428 strain

| Composition | Compound C PIPC/TAZ* | Compound C AMK |
|---|---|---|
| FIC index | 0.63 | 0.75 |

*TAZ = 4 µg/mL

TABLE 22

*Escherichia coli* TK-1537 strain

| Composition | Compound C CFPM | Compound C MEPM |
|---|---|---|
| FIC index | 0.56 | 0.75 |

TABLE 23

*Stenotrophomonas maltophilia* NBRC13692 strain

| Composition | Compound C CFPM | Compound C MEPM | Compound C AMK |
|---|---|---|---|
| FIC index | 0.75 | ≤0.75 | 0.63 |

TABLE 24

*Acinetobacter baumannii* BAA-1791 strain

| Composition | Compound C CFPM | Compound C MEPM | Compound C IPM | Compound C LVFX | Compound C AMK | Compound C VCM |
|---|---|---|---|---|---|---|
| FIC index | ≤0.08 | ≤0.08 | ≤0.09 | ≤0.56 | ≤0.19 | ≤0.05 |

The combinations of Compound A, B or C with the antimicrobial substances exhibited better antimicrobial activity against the *Pseudomonas aeruginosa* S-3097 strain, the *Pseudomonas aeruginosa* S-2994 strain, which is carbapenem-resistant, and *Acinetobacter baumannii*, which is multidrug-resistant, than Compound A, B or C singly. The combinations of Compound A B, or C with the antimicrobial substances exhibited better antimicrobial activity also against *Klebsiella pneumoniae*, *Escherichia coli*, and *Stenotrophomonas maltophilia* than Compound A, B or C singly.

As clearly seen from the above results, the combinations of Compounds A, B and C or a salt thereof with various antimicrobial substances exhibit synergistic antimicrobial activity and are effective for treatment of infections caused by Gram-negative bacteria.

Test Example 3 Test on Inhibition of Vero Cell Growth

Compound A, Compound B and Compound C were used as a test compound.

Each test compound was dissolved in dimethyl sulfoxide, adjusted to each concentration using E'MEM, and then dispensed at 0.1 mL/well to 96-well microplates. The Vero cell suspension was prepared at $3 \times 10^4$ cells/mL using E'MEM supplemented with 20% FBS, inoculated thereto at 0.1 mL/well, and cultured at 37° C. for 3 days under 5% $CO_2$. At the completion of the culture, PBS supplemented with 1 mg/mL 2,3-bis-(2-methoxy-4-nitro-5-sulfophenyl)-5-((phenylamino)carbonyl)-2H-tetrazolium inner salt monosodium salt (XTT) and 25 µM phenazine methosulfate (PMS) was prepared and added thereto at 50 µL/well. Approximately 2 hours later, the absorbance at 450 nm was measured using a microplate reader.

The absorbance ratio between a test compound-non-supplemented control and each well was calculated to calculate the concentration at which the compound inhibited 50% of cell growth ($CC_{50}$; µg/mL).

As a result, all the $CC_{50}$s of the test compounds were 100 µg/mL or more.

Test Example 4 Evaluation of hERG Inhibitory Activity

Compound A and Compound C were used as a test compound.

HEK 293 cells (human embryo kidney 293 cells, Cytomyx LLC) transfected with hERG gene (human ether-a-go-go related gene) were used.

The culture solution used was a MEM medium containing 10% fetal bovine serum and 1% non-essential amino acid and further supplemented with Geneticin at a concentration of 400 µg/mL. The cells were cultured in a carbonic acid gas incubator (37.0° C., 5% $CO_2$).

The hERG current was measured by a whole cell clamp method. A glass cover with the cells for measurement attached thereto was placed in a dish and perfused at a rate of 2 mL/min with a perfusate (composition: 137 mmol/L NaCl, 4 mmol/L KCl, 10 mmol/L HEPES, 1.8 mmol/L $CaCl_2$, 1 mmol/L $MgCl_2$, 10 mmol/L glucose, pH 7.4). The inside temperature of the perfusion chamber was kept at 25° C. The cells were contacted with a glass electrode (2.0 to 8.0 MΩ) charged with an internal solution (composition: 130 mmol/L KCl, 1 mmol/L $MgCl_2$, 5 mmol/L EGTA, 10 mmol/L HEPES, 5 mmol/L MgATP, pH 7.2) to break the patch membranes, followed by the measurement of the hERG current using a patch clamp amplifier (EPC-7 Plus, HEKA) via patch clamp software pClamp 10 (Molecular Devices Corporation). The pulse protocol involved a holding potential of −80 mV, a depolarizing pulse of +20 mV for 1.5 seconds and a repolarizing pulse of −50 mV for 1.5 seconds. After confirmation that a stable current waveform was obtained, each test compound was applied thereto.

Before the application and 10 minutes after the application, the peak value of tail current in the hERG current waveform was analyzed to calculate the ratio of the value 10 minutes after the application to the value before the application (relative value, %).

As a result, none of the test compounds exhibited an hERG inhibitory activity up to 300 μmol/L.

Test Example 5 In Vitro Micronucleus Test for Examining the Presence or Absence of Genotoxicity Compound A was used as a test compound.

In order to examine the inducibility of the chromosomal aberrations by each test compound in cultured cells, the in vitro micronucleus test was carried out. This test was carried out by a short-time treatment method (in the presence and absence of a metabolic activation) and a 30-hour treatment method using Chinese hamster lung fibroblasts (CHL/IU cells). The concentration of the test compound was set to 1.00 mmol/L as the maximum dose with reference to the "Guidance on Genotoxicity Testing and Data Interpretation for Pharmaceuticals Intended for Human Use". Specimens were observed as to doses of 0.25, 0.50 and 1.00 mmol/L.

The cells were inoculated at $15 \times 10^4$ cells to a 60-mm dish (IWAKI) and precultured at 37° C. for 24 hours under 5% $CO_2$ using a MEM medium (Sigma-Aldrich Co., Ltd.) containing 10% newborn calf serum (Sigma-Aldrich Co., Ltd.) and 50 U/mL-50 μg/mL Penicillin-Streptomycin (Sigma-Aldrich Co., Ltd.). After the completion of the preculture, a vehicle (DMSO) or each test compound was added thereto. In the short-time treatment method, 6 hours after the culture, the cells were washed with PBS(−) (Sigma-Aldrich Co., Ltd.), and then, the medium was replaced with a fresh medium, followed by further culture for 24 hours. In the 30-hour treatment method, after the addition of the test compound, the cells were cultured for 30 hours. After the completion of the culture, the cells were dissociated using a 0.05% trypsin-EDTA solution (Sigma-Aldrich Co., Ltd.). After centrifugation, the supernatant was removed, and 3 mL of a 0.075 mol/L aqueous potassium chloride solution was added to the cells. After hypotonic treatment at room temperature for 5 minutes, the cells were fixed with an ice-cold fixing solution (methanol:acetic acid=19:1) to prepare a glass slide specimen (giemsa-stained (Merck)). Two thousand cells per dose were observed to measure the number of cells having the micronucleus. When the frequency of appearance of the micronucleus in the test compound group was significantly increased as compared with the vehicle control group, the test compound was confirmed to be positive. When this frequency of appearance was equivalent to that of the vehicle control, the test compound was confirmed to be negative.

As a result, in either treatment method, the test compound was negative at the dose of 1 mmol/L or less.

Test Example 6 Measurement of Binding Ratio to Plasma Protein

Compound A and Compound C were used as a test compound.

Each test compound was added to human serum to prepare a 1 μg/mL spiked serum, which was then left standing at room temperature for 1 hour or longer. A filtrate (20 μL) was collected by a centrifugal ultrafiltration method (molecular weight cutoff: 10,000, 1500×g, 25° C., 10 min), then human serum and an internal standard solution (furosemide-acetonitrile solution) were added thereto. To the compound-spiked serum, PBS and an internal standard solution were added. Each mixture was stirred and then centrifuged, and the concentration in the supernatant was determined by LC-MS/MS.

The ratio of protein binding was determined according to the following calculation expression:

Ratio of protein binding (%)=(1−(Concentration of the filtrate)/(Concentration of the compound-spiked serum))×100

As a result, all the protein binding ratios of the test compounds were 80% or less.

Test Example 7 Inhibitory Effect on Liver Drug-Metabolizing Enzyme in Human

Compound A and Compound C were used as a test compound.

Pooled human liver microsomes were used. Substrates and their final concentrations as well as the positive controls and their final concentrations were as described in Tables 25 and 26. The reaction was carried out in a phosphate buffer solution (100 mmol/L, pH 7.4), and the final concentrations of the reaction system were set to 0.5 mg/mL human liver microsome protein, 1.55 mmol/L oxidized form of nicotinamide adenine dinucleotide phosphate (NADP+), 3.3 mmol/L glucose-6-phosphate, 3.3 mmol/L magnesium chloride and 0.4 Units/mL glucose-6-phosphate dehydrogenase (G6PDH). The final concentration of each compound in the reaction solution was set to 100 μM. Each of these reaction solutions was incubated at 37° C. for 30 minutes. Then, the substrates were added thereto and reacted at 37° C. for 10 minutes. The reaction was terminated by the addition of a 1.5-fold volume of an internal standard solution (acetonitrile solution containing 0.25 mmol/L dextrorphan and 2% formic acid). Then, the solution was centrifuged, and the concentration of metabolites in the supernatant was determined by LC-MS/MS.

The ratio of inhibitory activity by addition of the inhibitor was determined according to the following calculation expression:

Ratio of inhibitory activity (%)=(1−(Concentration of CYP metabolites in the presence of the test compound)/(Concentration of CYP metabolites in the absence of the test compound))×100

As a result, all the inhibitory activity ratios of the test compounds were 30% or less.

TABLE 25

| Molecular species | Substrate name | Final concentration (μmol/L) |
|---|---|---|
| CYP1A2 | Phenacetin | 10 |
| CYP2C8 | Amodiaquine | 0.2 |
| CYP2C9 | Tolbutamide | 100 |
| CYP2C19 | (S)-Mephenytoin | 40 |
| CYP2D6 | (±)-Bufuralol | 4 |
| CYP3A4 | Midazolam | 1 |
| CYP3A4 | Testosterone | 5 |

TABLE 26

| Molecular species | Positive control | Final concentration (μmol/L) |
|---|---|---|
| CYP1A2 | Furafyline | 10 |
| CYP2C8 | Quercetin | 10 |
| CYP2C9 | Tienilic acid | 1 |
| CYP2C19 | Ticlopidine | 1 |
| CYP2D6 | Paroxetine | 2 |
| CYP3A4 | Verapamil | 10 |

Subsequently, Production Examples of the compounds used in the present invention will be described, but the present invention is not limited to these.

Unless specifically mentioned, the silica gel column chromatography is flash column chromatography, and its carrier is B.W. silica gel BW-300, Fuji Silysia Chemical Ltd.

The mixture ratio in the eluant is the volume ratio.

Each abbreviation has the following meaning.

DMSO-$d_6$: Heavy dimethyl sulfoxide

ESI: Electrospray ionization

IPE: Diisopropyl ether

Me: Methyl

TBS: tert-Butyldimethylsilyl

THP: Tetrahydro-2H-pyran-2-yl s: Singlet d: Doublet dd: Double doublet m: Multiplet In an NMR spectrum, for example, the description of [1.81], 1.82 (3H, s) indicates that peaks derived from each diastereomer in a diastereomer mixture are observed at 1.81 and 1.82 as a singlet, and the total number of protons is 3H.

Production Example 1

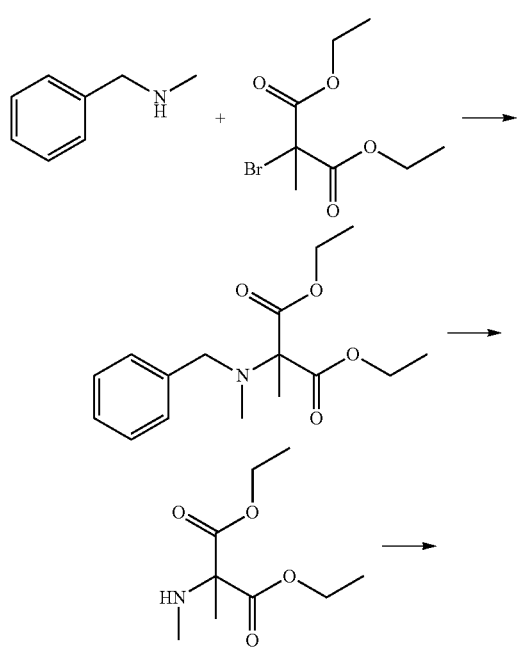

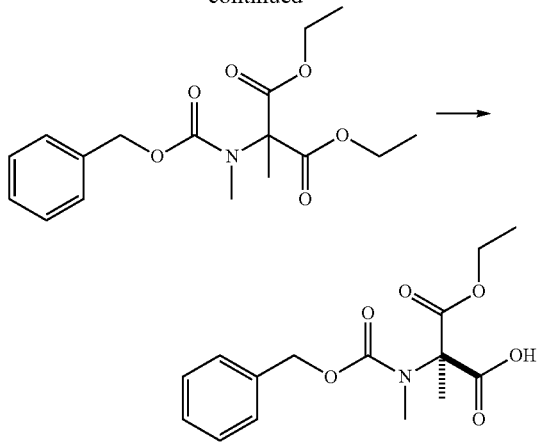

To 1000 mL of N-methylpyrrolidone, 421 g of N-methylbenzylamine and 400 g of diethyl 2-bromo-2-methylmalonate were added and stirred at 100° C. for an hour. Then, the reaction mixture was cooled. After 1.5 L of toluene and 1.5 L of water were added sequentially, 70 mL of hydrochloric acid was added. The organic layer was separated, and the solvent was distilled off under reduced pressure to obtain 499 g of a colorless oily product.

To 400 g of the obtained oily product, 2.0 L of ethyl acetate, 32 g of 10% palladium on carbon (50% wet) and 81.9 g of acetic acid were added sequentially and stirred under hydrogen atmosphere (0.5 MPa) at 45° C. for 18 hours and 30 minutes. After the reaction mixture was cooled and filtered over celite, the residue was washed with 400 mL of ethyl acetate. To the filtrate, 1200 mL of water was added. Hydrochloric acid was used to adjust the pH to 2 or less, and the aqueous layer was separated. To the obtained aqueous layer, 1200 mL of ethyl acetate was added, and a 20% sodium hydroxide aqueous solution was used to adjust the pH to 9. The organic layer was separated and the solvent was distilled off under reduced pressure to obtain 204 g of a colorless oily product.

To 200 g of the obtained oily product, 1.0 L of acetonitrile and 198 g of sodium hydrogen carbonate were added. Then, 168 g of benzyl chloroformate was added dropwise under ice cooling over 25 minutes. The reaction mixture was warmed to room temperature, stirred for 7 hours and 45 minutes, and allowed to stand overnight. Then, the reaction mixture was stirred at 40 to 45° C. for 1 hour and 30 minutes, and cooled, and then, an insoluble material was filtered off. The residue was washed with 200 mL of acetonitrile. The filtrate and the washed solution were combined and concentrated under reduced pressure to obtain 324 g of a colorless oily product.

To 1968 mL of water, 15.36 g of sodium dihydrogen phosphate dihydrate was added, and 1125 mL of a 0.05 mol/L sodium hydroxide aqueous solution was added. To this aqueous solution, a mixture of 120 g of the obtained oily product and 360 mL of acetonitrile was added at 24° C., stirred at the same temperature for 2 hours and 45 minutes, and then, allowed to stand overnight. Additionally, the reaction mixture was stirred at the same temperature for 6 hours, and then, allowed to stand for 22 hours. Subsequently, 30 mL of a 0.05 mol/L phosphate buffer solution (pH 7.4) was added to 2.9 g (20 units/mg) of porcine liver esterase and subjected to ultrasonic irradiation for 30 minutes to provide a suspension solution, which was added to the reaction mixture at 25° C. The reaction mixture, of which pH was adjusted with a 1 mol/L sodium hydroxide aqueous solution within the range of 6.7 to 7.1, was stirred at 26° C. for 5 hours. To the reaction mixture, 1200 mL of ethyl acetate was added, and 37 mL of hydrochloric acid, 300 g of sodium chloride and 48 g of Celpure were added sequentially under ice cooling. After stirring at the same temperature for an hour, an insoluble material was filtered off. The residue was washed with 240 mL of ethyl acetate, and the filtrate and the washed solution were combined. The organic layer was separated, and the aqueous layer was extracted with 180 mL of ethyl acetate. The organic layer and the extract solution were combined, and 48 g of anhydrous sodium sulfate and 1.2 g of activated carbon were added. After stirring for 30 minutes, the mixture was filtered over celite. The residue was washed with 180 mL of ethyl acetate, and the filtrate and the washed solution were combined. Then, 1540 mL of the solvent was distilled off under reduced pressure. To the obtained residue, 240 mL of heptane was added and cooled to 18° C. over 2 hours. The solid material was collected by filtration and washed with 120 mL of heptane twice to obtain 88.18 g (>99.9% ee) of (((((2R)-2-carboxy-1-ethoxy-1-oxopropan-2-yl)(methyl)carbamoyl)oxy)methyl)benzene as colorless crystals.

$^1$H-NMR (400 MHz, DMSO-d$_6$) δ: 1.15-1.20 (3H, m), 1.61 (3H, s), 2.86 (3H, s), 3.95-4.15 (2H, m), 5.07 (2H, s), 7.28-7.43 (5H, m)

HPLC Measurement Conditions

Column: 4.6×150 mm CHIRALPAK IA 5 μm

Measurement wavelength: 210 nm

Column temperature: 40° C.

Mobile phase: hexane:ethanol=95:5 (0.1% trifluoroacetic acid)

Flow rate: 0.7 mL/minute

Production Example 2

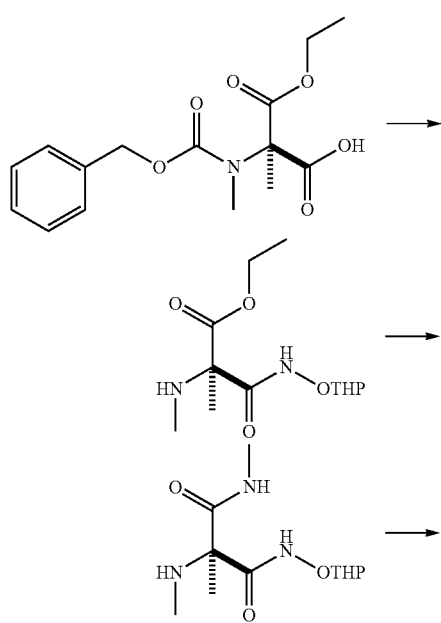

-continued

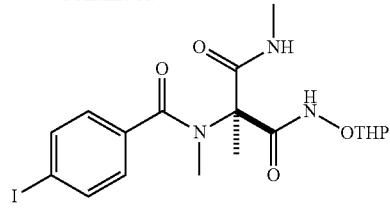

To 250 g of (((((2R)-2-carboxy-1-ethoxy-1-oxopropan-2-yl)(methyl)carbamoyl)oxy)methyl)benzene, 1300 mL of ethyl acetate and 1.0 mL of N,N-dimethylformamide were added. After 133 g of oxalyl chloride was added dropwise at 5° C. over 20 minutes, 200 mL of ethyl acetate was added. The reaction mixture was warmed to 20° C. and stirred for 4 hours. Under reduced pressure, 1395 mL of the solvent was distilled off. To the obtained residue, 1000 mL of tetrahydrofuran was added and cooled to 8° C. At the same temperature, 94.1 g of triethylamine and 109 g of O-(tetrahydro-2H-pyran-2-yl)hydroxylamine were added sequentially, and warmed to 20° C. over 3 hours with stirring. After the reaction mixture was allowed to stand overnight, 225 mL of acetone was added and stirred for 40 minutes. Subsequently, 750 mL of toluene and 1000 mL of water were added and cooled to 10° C. Then 62 mL of hydrochloric acid was added. Additionally, the pH was adjusted to 3 with 6 mol/L hydrochloric acid and a 20% sodium hydroxide aqueous solution, and the aqueous layer was separated. To the obtained aqueous layer, 1250 mL of ethyl acetate was added, and 210 mL of a 20% sodium hydroxide aqueous solution was added. Subsequently, 1450 g of sodium chloride was added, and the resultant solution was warmed to 30° C. The organic layer was separated, and the aqueous layer was extracted with 750 mL of ethyl acetate. The organic layer and the extract solution were combined, and the solvent was distilled off under reduced pressure. To the obtained residue, 250 mL of toluene was added. The solvent was distilled off under reduced pressure to obtain 215 g of an orange oily product.

To 213 g of the obtained oily product, a 40% methylamine/methanol solution was added at room temperature, stirred at 40 to 43° C. for 8 hours and 30 minutes, and then, allowed to stand overnight. Additionally, after stirring at 45° C. for 5 hours, the solvent was distilled off under reduced pressure. To the obtained residue, toluene was added, and the solvent was distilled off under reduced pressure. Subsequently, tetrahydrofuran was added to the obtained residue, and the solvent was distilled off under reduced pressure to obtain 203 g of a yellow oily product.

To 203 g of the obtained oily product, 1400 mL of tetrahydrofuran was added, and 117 g of sodium hydrogen carbonate was added at 35° C. Subsequently, a mixture of 168 g of 4-iodobenzoyl chloride and 200 mL of tetrahydrofuran, and 100 mL of tetrahydrofuran were added at the same temperature and stirred for 5 hours. After 58.2 g of sodium hydrogen carbonate and 29 mL of morpholine were added to the reaction mixture at the same temperature and stirred for 2 hours, the mixture was allowed to stand overnight at room temperature. To the reaction mixture, 1370 mL of ethyl acetate, 1700 mL of water and 170 g of sodium chloride were added sequentially, and the organic layer was separated. After 860 mL of water and 42.7 g of sodium chloride were added to the obtained organic layer and stirred for 15 minutes, the organic layer was separated. The obtained organic layer was filtered, and the solvent of the filtrate was distilled off under reduced pressure. After 300 mL of ethyl acetate and 300 mL of toluene were added to the obtained residue and stirred at 30° C. for an hour, the mixture was allowed to stand overnight. The solid was filtered off and washed with an ethyl acetate/toluene mixture (1:1, 300 mL) to obtain 206 g of a brown solid. After 2000 mL of ethyl acetate was added to the obtained brown solid and stirred at 40° C. for an hour, the mixture was cooled under ice cooling, and the solid material was collected by filtration. The solid was washed with ethyl acetate to obtain 148.9 g (>99.9% ee) of (2S)-2-((4-iodobenzoyl)(methyl)amino)-N,2-dimethyl-N'-(tetrahydro-2H-pyran-2-yloxy)malonamide as colorless crystals.

$^1$H-NMR (400 MHz, DMSO-$d_6$) δ: 1.40-1.75 (6H, m), 1.61 (3H, s), [2.62] 2.63 (3H, d, J=3.7 Hz), 2.99 (3H, d, J=2.7 Hz), 3.40-3.60 (1H, m), [3.82-3.92] 3.92-4.02 (1H, m), [4.74-4.80] 4.80-4.86 (1H, m), [7.31] 7.33 (2H, d, J=8.2 Hz), 7.85 (2H, d, J=8.3 Hz), [8.25-8.33] 8.35-8.43 (1H, m), 11.52 (1H, s)

HPLC Measurement Conditions
 Column: 4.6×250 mm CHIRALPAK ID 5 μm
 Measurement wavelength: 230 nm
 Column temperature: 40° C.
 Mobile phase: hexane:ethanol=85:15
 Flow rate: 1.0 mL/minute Production Example 3

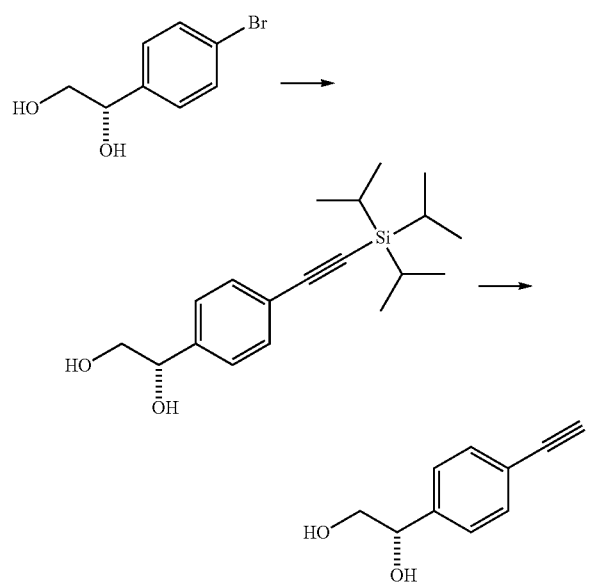

To a mixture of 1.08 g of (1S)-1-(4-bromophenyl)ethane-1,2-diol, 350 mg of bis-triphenylphosphinepalladium(II) dichloride, 190 mg of copper(I) iodide, and 10 mL of n-butyl acetate, 7.8 mL of triisopropylsilylacetylene and 7.0 mL of triethylamine were added under a nitrogen atmosphere, and the resulting mixture was stirred under reflux for 1 hour. The reaction mixture was cooled, a saturated aqueous solution of ammonium chloride was added, the pH was adjusted to 6.2 with 6 mol/L hydrochloric acid, then Celpure and ethyl acetate were added, and then the insoluble material was filtered off. The organic layer of the filtrate was separated, washed with a saturated aqueous solution of sodium chloride, and then dried over anhydrous magnesium sulfate. The solvent was distilled off under reduced pressure, and the obtained residue was subjected to silica gel column chromatography [eluent; ethyl acetate:hexane=40:60→45:55] to obtain 1.32 g of a yellow oil.

To a mixture of 1.32 g of the obtained yellow oil and 13 mL of tetrahydrofuran, 6.2 mL of a 1 mol/L solution of tetra-n-butylammonium fluoride in tetrahydrofuran was added under ice cooling, and the resulting mixture was stirred at the same temperature for 30 minutes and then at room temperature for 45 minutes. A saturated aqueous solution of ammonium chloride was added to the reaction mixture, the pH was adjusted to 2.0 with 1 mol/L hydrochloric acid, and then ethyl acetate was added. The organic layer was separated, and the aqueous layer was extracted with ethyl acetate twice. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=50:50→70:30] to obtain 513 mg of a light brown solid. Hexane was added thereto, and the solid material was collected by filtration to obtain 466 mg of (1S)-1-(4-ethynylphenyl)ethane-1,2-diol as a light brown solid.

$^1$H-NMR (400 MHz, CDCl$_3$) δ: 1.97-2.07 (1H, m), 2.56 (1H, d, J=3.4 Hz), 3.08 (1H, s), 3.56-3.70 (1H, m), 3.71-3.82 (1H, m), 4.79-4.88 (1H, m), 7.34 (2H, d, J=8.3 Hz), 7.49 (2H, d, J=8.3 Hz)

Production Example 4

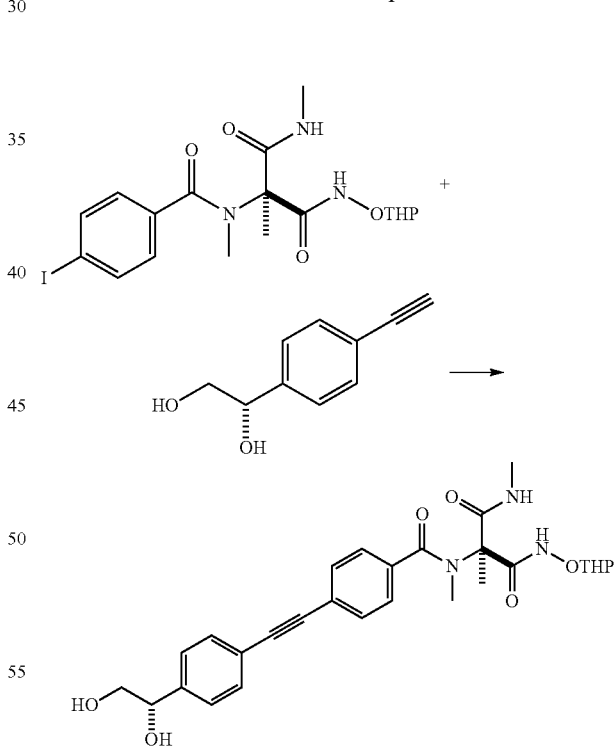

To a mixture of 587 mg of (2S)-2-((4-iodobenzoyl)(methyl)amino)-N,2-dimethyl-N'-(tetrahydro-2H-pyran-2-yloxy)malonamide, 253 mg of (1S)-1-(4-ethynylphenyl)ethane-1,2-diol, 84 mg of bis-triphenylphosphinepalladium(II) dichloride, 46 mg of copper(I) iodide, and 6.0 mL of tetrahydrofuran, 0.59 mL of triethylamine was added under a nitrogen atmosphere and under ice cooling, and the resulting mixture was stirred at the same temperature for 2 hours.

A saturated aqueous solution of ammonium chloride and ethyl acetate were added to the reaction mixture, and the pH was adjusted to 6.4 with 1 mol/L hydrochloric acid. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=40:60] to obtain 767 mg of (2S)-2-((4-((4-((1S)-1,2-dihydroxyethyl)phenyl)ethynyl)benzoyl)(methyl)amino)-N2-dimethyl-N'-(tetrahydro-2H-pyran-2-yloxy)malonamide as a pale yellow foamy solid.

$^{1}$H-NMR (400 MHz, CDCl$_{3}$) δ: 1.50-1.68 (3H, m), 1.71-1.92 (3H, m), [1.82], 1.83 (3H, s), 2.08-2.14 (1H, m), 2.63-2.68 (1H, m), [2.86], 2.87 (3H, d, J=4.1 Hz), [3.17], 3.20 (3H, s), 3.53-3.83 (3H, m), 3.83-4.07 (1H, m), 4.83-4.89 (1H, m), 4.93-5.03 (1H, m), 7.37 (2H, d, J=8.0 Hz), 7.48-7.61 (6H, m), [6.97-7.04], 7.61-7.67 (1H, m), [10.10], 10.51 (1H, s)

Production Example 5

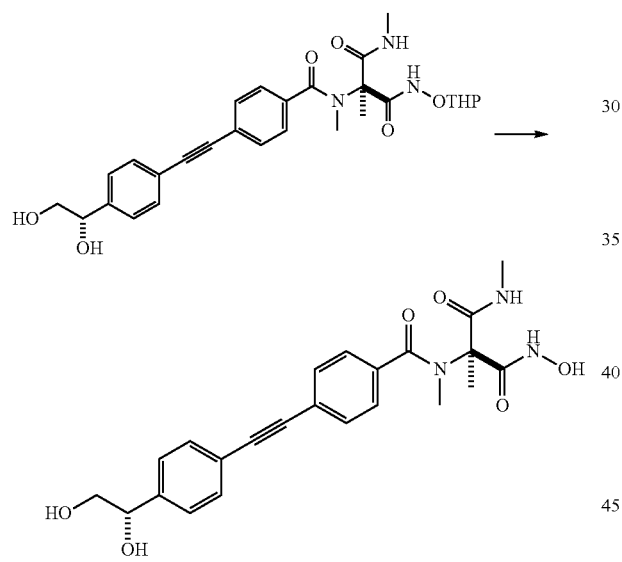

To a mixture of 767 mg of (2S)-2-((4-((4-((1S)-1,2-dihydroxyethyl)phenyl)ethynyl)benzoyl)(methyl)amino)-N,2-dimethyl-N'-(tetrahydro-2H-pyran-2-yloxy)malonamide and 6.0 mL of methanol, 46 mg of p-toluenesulfonic acid monohydrate was added under ice cooling, and the resulting mixture was stirred at the same temperature for 40 minutes and then at room temperature for 1 hour. Water and ethyl acetate were added to the reaction mixture, and the resulting mixture was neutralized with a saturated aqueous solution of sodium hydrogen carbonate. The organic layer was separated, ethyl acetate and sodium chloride were added to the aqueous layer, and the solid material was collected by filtration. The organic layer of the filtrate was separated, ethyl acetate and sodium chloride were added to the aqueous layer, and the solid material was collected by filtration. The organic layer of the filtrate was separated, the organic layer and the solid material thus obtained were combined together, and then the solvent was distilled off under reduced pressure. The obtained residue was purified by silica gel column chromatography [eluent; methanol:chloroform=10:90→15:85] to obtain 585 mg of a yellow foamy solid. Ethyl acetate and IPE were added thereto, and the solid material was collected by filtration to obtain 463 mg of (2S)-2-((4-((4-((1S)-1,2-dihydroxyethyl)phenyl)ethynyl)benzoyl)(methyl)amino)-N-hydroxy-N',2-dimethylmalonamide (Compound A) as a yellow solid.

$^{1}$H-NMR (400 MHz, CD$_{3}$OD) δ: 1.77 (3H, s), 2.79 (3H, s), 3.17 (3H, s), 3.55-3.68 (2H, m), 4.67-4.74 (1H, m), 7.41 (2H, d, J=8.3 Hz), 7.51 (2H, d, J=8.3 Hz), 7.55 (2H, d, J=8.5 Hz), 7.68 (2H, d, J=8.5 Hz); MS (ESI): 462[M+Na]$^{+}$, 438 [M-H]$^{-}$

Production Example 6

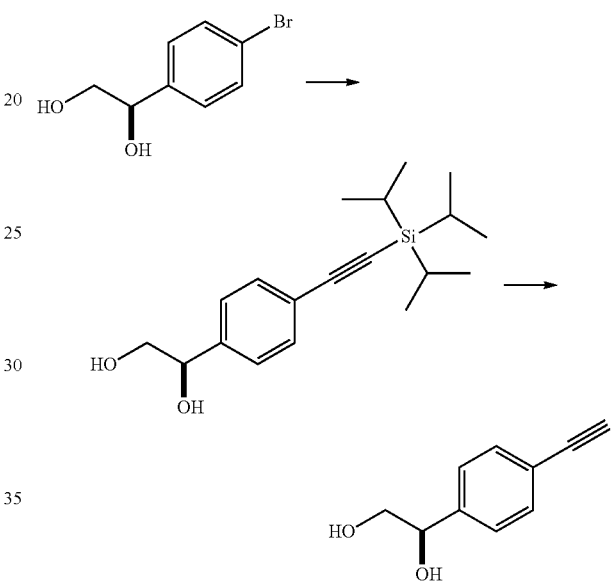

In the same manner as in Production Example 3, from 1.09 g of (1R)-1-(4-bromophenyl)ethane-1,2-diol, 558 mg of (1R)-1-(4-ethynylphenyl)ethane-1,2-diol was obtained as a white solid.

(400 MHz, CDCl$_{3}$) δ: 2.00 (1H, dd, J=7.1, 4.9 Hz), 2.54 (1H, d, J=3.4 Hz), 3.08 (1H, s), 3.60-3.68 (1H, m), 3.73-3.81 (1H, m), 4.80-4.88 (1H, m), 7.34 (2H, d, J=8.1 Hz), 7.49 (2H, d, J=8.0 Hz)

Production Example 7

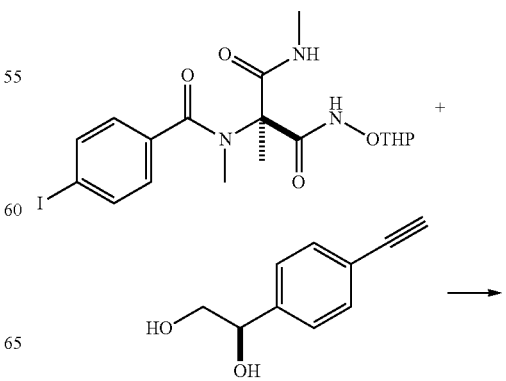

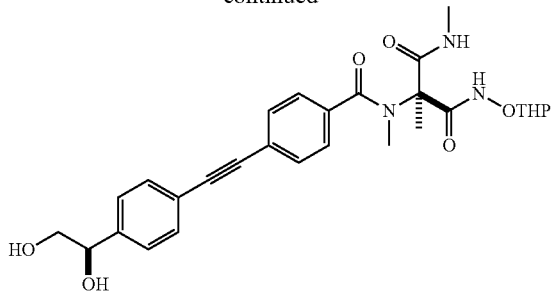

In the same manner as in Production Example 4, from 587 mg of (2S)-2-((4-iodobenzoyl)(methyl)amino)-N,2-dimethyl-N'-(tetrahydro-2H-pyran-2-yloxy)malonamide and 291 mg of (1R)-1-(4-ethynylphenyl)ethane-1,2-diol, 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide was obtained as a light brown foamy solid.

$^1$H-NMR (400 MHz, CDCl$_3$) δ: 1.53-1.69 (3H, m), 1.76-1.92 (3H, m), [1.81], 1.82 (3H, s), 2.27-2.37 (1H, m), 2.83-2.91 (4H, m), [3.17], 3.19 (3H, s), 3.53-3.83 (3H, m), [3.83-3.92], 3.98-4.08 (1H, m), 4.81-4.88 (1H, m), 4.94-5.04 (1H, m), 7.35 (2H, d, J=8.1 Hz), 7.45-7.59 (6H, m), [6.96-7.06], 7.59-7.68 (1H, m), [10.14], 10.56 (1H, s)

Production Example 8

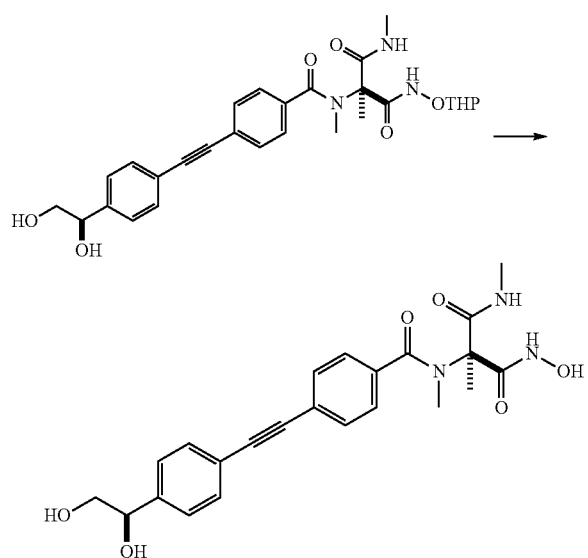

To a mixture of 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide and 6.3 mL of methanol, 46 mg of p-toluenesulfonic acid monohydrate was added under ice cooling, and the resulting mixture was stirred at the same temperature for 30 minutes and then at room temperature for 45 minutes. Water and ethyl acetate were added to the reaction mixture, and the resulting mixture was neutralized with a saturated aqueous solution of sodium hydrogen carbonate. The organic layer was separated, and the aqueous layer was extracted with ethyl acetate twice. Sodium chloride was added to the aqueous layer, and the solid material was collected by filtration. Sodium chloride and ethyl acetate were added to the filtrate, and the solid material was collected by filtration. The organic layer of the filtrate was separated, the organic layer, the extract, and the solid material thus obtained were combined together, and then the solvent was distilled off under reduced pressure. The obtained residue was purified by silica gel column chromatography [eluent; methanol:chloroform=10:90→15:85] to obtain 556 mg of a yellow foamy solid. Ethyl acetate and IPE were added thereto, and the solid material was collected by filtration to obtain 458 mg of (2S)-2-((4-((4-((1R)-1,2-dihydroxyethyl)phenyl)ethynyl)benzoyl)(methyl)amino)-N-hydroxy-N',2-dimethylmalonamide (Compound B) as a yellow solid.

$^1$H-NMR (400 MHz, CD$_3$OD) δ: 1.78 (3H, s), 2.80 (3H, s), 3.17 (3H, s), 3.57-3.67 (2H, m), 4.68-4.74 (1H, m), 7.42 (2H, d, J=8.3 Hz), 7.52 (2H, d, J=8.3 Hz), 7.56 (2H, d, J=8.6 Hz), 7.61 (2H, d, J=8.6 Hz); MS (ESI): 462[M+Na]$^+$, 438[M-H]$^-$

Production Example 9

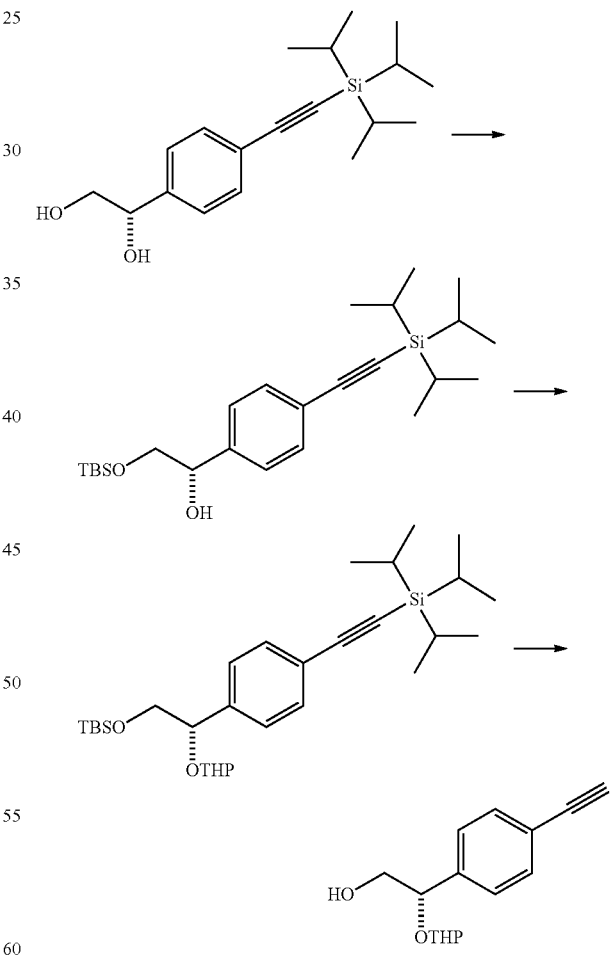

To a mixture of 2.79 g of (1S)-1-(4-((triisopropylsilyl)ethynyl)phenyl)ethane-1,2-diol, 28 mL of dichloromethane, 2.7 mL of triethylamine, and 213 mg of N,N-dimethylaminopyridine obtained in the same manner as in Production Example 3, 1.45 g of tert-butyldimethylsilyl chloride was added under a nitrogen atmosphere and under ice cooling, and the resulting mixture was stirred at room temperature for 2 hours, and then was allowed to stand at the same temperature overnight. A saturated aqueous solution of ammonium chloride and ethyl acetate were added to the reaction mixture, and the pH was adjusted to 4.0 with 6 mol/L hydrochloric acid. The organic layer was separated, washed with a saturated aqueous solution of sodium chloride, and then dried over anhydrous magnesium sulfate. The solvent was distilled off under reduced pressure to obtain 3.70 g of a brown oil.

To 3.70 g of the obtained brown oil, 28 mL of dichloromethane and 439 mg of pyridinium p-toluenesulfonate were added, 2.4 mL of 3,4-dihydro-2H-pyran was added under ice cooling, and then the resulting mixture was stirred at room temperature for 5 hours. To the reaction mixture, 3.0 mL of triethylamine was added, and the solvent was distilled off under reduced pressure. Water and ethyl acetate were added to the obtained residue. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; diethyl ether:hexane=10:90] to obtain 3.65 g of a yellow oil.

To 3.65 g of the obtained yellow oil, 18 mL of tetrahydrofuran was added, then 17 mL of a 1 mol/L solution of tetra-n-butylammonium fluoride in tetrahydrofuran was added under ice cooling, and the resulting mixture was stirred at room temperature for 1 hour. A saturated aqueous solution of ammonium chloride and ethyl acetate were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=30:70→40:60] to obtain 1.78 g of (2S)-2-(4-ethynylphenyl)-2-(tetrahydro-2H-pyran-2-yloxy)ethanol as a white solid.

$^1$H-NMR (400 MHz, CDCl$_3$) δ: 1.40-1.93 (6H, m), 2.11-2.20 (1H, m), [3.06], 3.07 (1H, s), 3.51-3.61 (1H, m), 3.62-3.76 (2H, m), [3.25-3.34], 3.92-4.07 (1H, m), [4.48-4.53], 4.79-4.86 (1H, m), [4.70-4.75], 4.87-4.93 (1H, m), [7.29], 7.35 (2H, d, J=8.3 Hz), 7.45 (2H, d, J=8.0 Hz)

Production Example 10

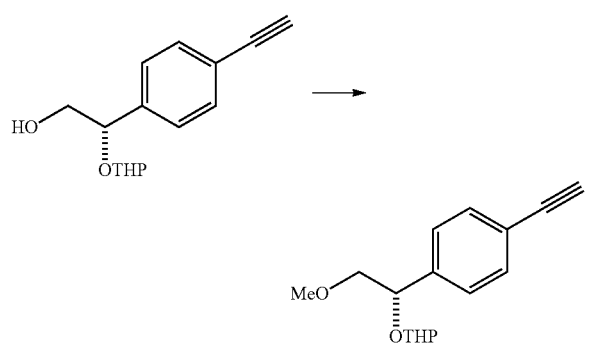

To a mixture of 800 mg of (2S)-2-(4-ethynylphenyl)-2-(tetrahydro-2H-pyran-2-yloxy)ethanol, 4.0 mL of dimethyl sulfoxide, and 0.4 mL of methyl iodide, 545 mg of potassium hydroxide was added under a nitrogen atmosphere and under ice cooling, and the resulting mixture was stirred at room temperature for 1 hour and 30 minutes. Toluene and a saturated aqueous solution of ammonium chloride were added to the reaction mixture, and the pH was adjusted to 6.1 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=10:90] to obtain 836 mg of 2-((1S)-1-(4-ethynylphenyl)-2-methoxyethoxy)tetrahydro-2H-pyran as a colorless oil.

$^1$H-NMR (400 MHz, CDCl$_3$) δ: 1.40-1.94 (6H, m), [3.05], 3.07 (1H, s), [3.36], 3.39 (3H, s), 3.45-3.56 (2H, m), [3.56-3.62], 3.62-3.69 (1H, m), [3.28-3.35], 3.97-4.06 (1H, m), [4.80-4.85], 4.91-4.97 (1H, m), [4.41-4.46], 4.97-5.01 (1H, m), [7.30], 7.37 (2H, d, J=8.4 Hz), 7.44-7.51 (2H, m)

Production Example 11

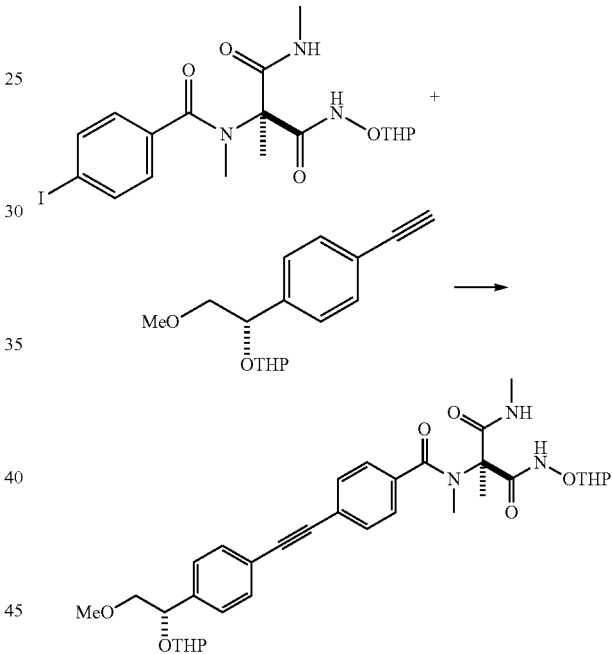

To a mixture of 478 mg of 2-((1S)-1-(4-ethynylphenyl)-2-methoxyethoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(11) dichloride, and 23 mg of copper(I) iodide, 0.51 mL of triethylamine was added under a nitrogen atmosphere and under ice cooling, and the resulting mixture was stirred at the same temperature for 2 hours and 30 minutes. A saturated aqueous solution of ammonium chloride and ethyl acetate were added to the reaction mixture, and the pH was adjusted to 6.0 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; acetone:chloroform=10:90] to obtain 485 mg of (2S)-2-((4-((4-((1S)-2-methoxy-1-(tetrahydro-2H-pyran-2-yloxy)ethyl)phenyl)

ethynyl)benzoyl)(methyl)amino)-N,2-dimethyl-N'-(tetrahydro-2H-pyran-2-yloxy)malonamide as a brown foamy solid.

$^1$H-NMR (400 MHz, CDCl$_3$) δ: 1.42-1.94 (12H, m), [1.81], 1.82 (3H, s), [2.85], 2.86 (3H, d, J=4.4 Hz), [3.17], 3.20 (3H, s), [3.37], 3.40 (3H, s), 3.47-3.72 (4H, m), [3.29-3.36], 3.83-3.91 (1H, m), 3.97-4.07 (1H, m), [4.43-4.48], 4.93-4.98 (1H, m), [4.84], 4.95 (1H, dd, J=7.3, 4.2 Hz), 4.98-5.03 (1H, m), [7.34], 7.41 (2H, d, J=8.3 Hz), 7.44-7.61 (6H, m), [6.96-7.04], 7.62-7.72 (1H, m), [10.01], 10.53 (1H, s)

Production Example 12

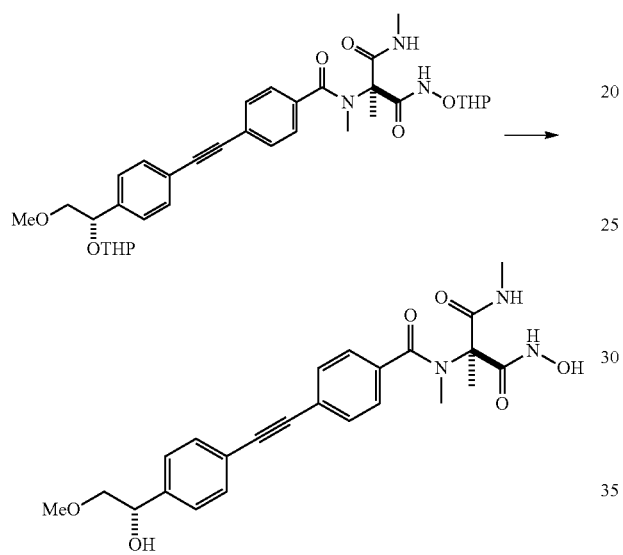

To a mixture of 485 mg of (2S)-2-((4-((4-((1S)-2-methoxy-1-(tetrahydro-2H-pyran-2-yloxy)ethyl)phenyl)ethynyl)benzoyl)(methyl)amino)-N,2-dimethyl-N'-(tetrahydro-2H-pyran-2-yloxy)malonamide and 4.8 mL of methanol, 23 mg of p-toluenesulfonic acid monohydrate was added under ice cooling, and the resulting mixture was stirred at the same temperature for 10 minutes and then at room temperature for 1 hour. Water and ethyl acetate were added to the reaction mixture, and the resulting mixture was neutralized with a saturated aqueous solution of sodium hydrogen carbonate. The organic layer was separated, and the obtained aqueous layer was extracted with ethyl acetate. Sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; methanol:chloroform=4:96→6:94] to obtain 288 mg of a brown solid. Ethyl acetate and IPE were added thereto, and the solid material was collected by filtration to obtain 240 mg of (2S)—N-hydroxy-2-((4-((4-((1S)-1-hydroxy-2-methoxyethyl)phenyl)ethynyl)benzoyl)(methyl)amino)-N',2-dimethylmalonamide (Compound C) as a brown solid.

$^1$H-NMR (400 MHz, CD$_3$OD) δ: 1.77 (3H, s), 2.79 (3H, s), 3.17 (3H, s), 3.37 (3H, s), 3.50 (2H, d, J=5.9 Hz), 7.41 (2H, d, J=8.3 Hz), 7.47-7.65 (6H, m); MS (ESI): 476[M+Na]$^+$, 452[M-H]$^-$

INDUSTRIAL APPLICABILITY

The pharmaceutical composition containing a hydroxamic acid derivative or a salt thereof and an antimicrobial substance has potent antimicrobial activity and is useful for treatment of Gram-negative bacterial infections.

The invention claimed is:

1. A pharmaceutical composition, comprising:
   (i) (2S)-2-((4-((4-((1 S)-1,2-dihydroxyethyl)phenyl)ethynyl)benzoyl)(methyl)amino)-N-hydroxy-N',2-dimethylmalonamide or a salt thereof, and
   (ii) at least one selected from the group consisting of (a) to (m):
   (a) a piperacillin/tazobactam combination agent, wherein (i) and (ii) exhibit a synergistic antimicrobial activity in the treatment of a bacterial infection caused by *Klebsiella pneumonia* or *Acinetobacter baumannii* BAA-1791;
   (b) cefepime, wherein (i) and (ii) exhibit a synergistic antimicrobial activity in the treatment of a bacterial infection caused by *Pseudomonas aeruginosa, Stenotrophomonas maltophilia, Stenotrophomonas maltophilia* or *Acinetobacter baumannii*;
   (c) ceftazidime, wherein (i) and (ii) exhibit a synergistic antimicrobial activity in the treatment of a bacterial infection caused by *Acinetobacter baumannii*;
   (d) meropenem, wherein (i) and (ii) exhibit a synergistic antimicrobial activity in the treatment of a bacterial infection caused by *Pseudomonas aeruginosa, Stenotrophomonas maltophilia* PM-171 or *Acinetobacter baumannii*;
   (e) imipenem, wherein (i) and (ii) exhibit a synergistic antimicrobial activity in the treatment of a bacterial infection caused by *Pseudomonas aeruginosa* S-2994 or *Acinetobacter baumannii*;
   (f) doripenem, wherein (i) and (ii) exhibit a synergistic antimicrobial activity in the treatment of a bacterial infection caused by *Acinetobacter baumannii*;
   (g) amikacin, wherein (i) and (ii) exhibit a synergistic antimicrobial activity in the treatment of a bacterial infection caused by *Pseudomonas aeruginosa* S-2994, *Klebsiella pneumonia, Stenotrophomonas maltophilia* PM-171 or *Acinetobacter baumannii*;
   (h) levofloxacin, wherein (i) and (ii) exhibit a synergistic antimicrobial activity in the treatment of a bacterial infection caused by *Escherichia coli*;
   (i) pazufloxacin, wherein (i) and (ii) exhibit a synergistic antimicrobial activity in the treatment of a bacterial infection caused by *Acinetobacter baumannii*;
   (j) ciprofloxacin, wherein (i) and (ii) exhibit a synergistic antimicrobial activity in the treatment of a bacterial infection caused by *Acinetobacter baumannii*;
   (k) vancomycin, wherein (i) and (ii) exhibit a synergistic antimicrobial activity in the treatment of a bacterial infection caused by *Acinetobacter baumannii*;
   (l) teicoplanin, wherein (i) and (ii) exhibit a synergistic antimicrobial activity in the treatment of a bacterial infection caused by *Acinetobacter baumannii*; and
   (m) lysozyme, wherein (i) and (ii) exhibit a synergistic antimicrobial activity in the treatment of a bacterial infection caused by *Acinetobacter baumannii*.

2. The pharmaceutical composition according to claim 1, comprising (a).

3. The pharmaceutical composition according to claim 2, wherein the *Klebsiella pneumonia* is *Klebsiella pneumonia* Y-891.

4. The pharmaceutical composition according to claim 1, comprising (b).

5. The pharmaceutical composition according to claim 4, wherein the *Pseudomonas aeruginosa* is *Pseudomonas aeruginosa* S-3097, the *Stenotrophomonas maltophilia* is *Stenotrophomonas maltophilia* NBRC13692, and the *Acinetobacter baumannii* is *Acinetobacter baumannii* BAA-1791 or *Acinetobacter baumannii* BAA-1794.

6. The pharmaceutical composition according to claim 1, comprising (c).

7. The pharmaceutical composition according to claim 6, wherein the *Acinetobacter baumannii* is *Acinetobacter baumannii* BAA-1791 or *Acinetobacter baumannii* BAA-1794.

8. The pharmaceutical composition according to claim 1, comprising (d).

9. The pharmaceutical composition according to claim 7, wherein the *Pseudomonas aeruginosa* is *Pseudomonas aeruginosa* S-3097, and the *Acinetobacter baumannii* is *Acinetobacter baumannii* BAA-1791 or *Acinetobacter baumannii* BAA-1794.

10. The pharmaceutical composition according to claim 1, comprising (e).

11. The pharmaceutical composition according to claim 1, wherein the *Acinetobacter baumannii* is *Acinetobacter baumannii* BAA-1791 or *Acinetobacter baumannii* BAA-1794.

12. The pharmaceutical composition according to claim 1, comprising (f).

13. The pharmaceutical composition according to claim 12, wherein the *Acinetobacter baumannii* is *Acinetobacter baumannii* BAA-1791.

14. The pharmaceutical composition according to claim 1, comprising (g).

15. The pharmaceutical composition according to claim 14, wherein the *Klebsiella pneumonia* is *Klebsiella pneumoniae* BAA1899, and the *Acinetobacter baumannii* is *Acinetobacter baumannii* BAA-1791 or *Acinetobacter baumannii* BAA-1794.

16. The pharmaceutical composition according to claim 1, comprising (h).

17. The pharmaceutical composition according to claim 16, wherein the *Escherichia coli* is *Escherichia coli* TK-1537.

18. The pharmaceutical composition according to claim 1, comprising (i).

19. The pharmaceutical composition according to claim 18, wherein the *Acinetobacter baumannii* is *Acinetobacter baumannii* BAA-1791.

20. The pharmaceutical composition according to claim 1, comprising (j).

21. The pharmaceutical composition according to claim 20, wherein the *Acinetobacter baumannii* is *Acinetobacter baumannii* BAA-1794.

22. The pharmaceutical composition according to claim 1, comprising (k).

23. The pharmaceutical composition according to claim 22, wherein the *Acinetobacter baumannii* is *Acinetobacter baumannii* BAA-1791.

24. The pharmaceutical composition according to claim 1, comprising (l).

25. The pharmaceutical composition according to claim 24, wherein the *Acinetobacter baumannii* is *Acinetobacter baumannii* BAA-1791 or *Acinetobacter baumannii* BAA-1794.

26. The pharmaceutical composition according to claim 1, comprising (m).

27. The pharmaceutical composition according to claim 26, wherein the *Acinetobacter baumannii* is *Acinetobacter baumannii* BAA-1794.

28. A method of treating a bacterial infection, comprising administering the pharmaceutical composition according to claim 1 to a subject in need thereof.

29. The method according to claim 28, wherein the bacterial infection is caused by *Klebsiella pneumonia* or *Acinetobacter baumannii* BAA-1791, and the pharmaceutical composition comprises (a).

30. The method according to claim 29, wherein the *Klebsiella pneumonia* is *Klebsiella pneumonia* Y-891.

31. The method according to claim 28, wherein the bacterial infection is caused by *Pseudomonas aeruginosa*, *Stenotrophomonas maltophilia*, *Klebsiella pneumonia*, or *Acinetobacter baumannii*, and the pharmaceutical composition comprises at least one selected from the group consisting of (b), (d), (e) and (g).

32. The method according to claim 31, wherein the *Pseudomonas aeruginosa* is *Pseudomonas aeruginosa* S-3097.

33. The method according to claim 31, wherein the *Pseudomonas aeruginosa* is *Pseudomonas aeruginosa* S-2994.

34. The method according to claim 31, wherein the *Stenotrophomonas maltophilia* is *Stenotrophomonas maltophilia* PM-171 or *Stenotrophomonas maltophilia* NBRC13692.

35. The method according to claim 31, wherein the *Acinetobacter baumannii* is *Acinetobacter baumannii* BAA-1791 or *Acinetobacter baumannii* BAA-1794.

36. The method according to claim 31, wherein the *Klebsiella pneumonia* is *Klebsiella pneumoniae* BAA1899.

37. The method according to claim 28, wherein the bacterial infection is caused by *Acinetobacter baumannii*, and the pharmaceutical composition comprises at least one selected from the group consisting of (c), (f), (i), (j), (k), (l) and (m).

38. The method according to claim 37, wherein the *Acinetobacter baumannii* is *Acinetobacter baumannii* BAA-1791 or *Acinetobacter baumannii* BAA-1794.

39. The method according to claim 28, wherein the bacterial infection is caused by *Escherichia coli*, and the pharmaceutical composition comprises (h).

40. The method according to claim 39, wherein the *Escherichia coli* is *Escherichia coli* TK-1537.

* * * * *